(12) United States Patent
Johnson

(10) Patent No.: US 7,022,142 B2
(45) Date of Patent: Apr. 4, 2006

(54) CONSTRAINED ACETABULAR LINER

(75) Inventor: Erin M. Johnson, Round Rock, TX (US)

(73) Assignee: Zimmer Austin, Inc., Austin, TX (US)

( * ) Notice: Subject to any disclaimer, the term of this patent is extended or adjusted under 35 U.S.C. 154(b) by 290 days.

(21) Appl. No.: 10/613,330

(22) Filed: Jul. 3, 2003

(65) Prior Publication Data

US 2005/0004677 A1    Jan. 6, 2005

(51) Int. Cl.
*A61F 2/32* (2006.01)

(52) U.S. Cl. .................................. 623/22.24

(58) Field of Classification Search .... 623/22.21–22.3, 623/22.17
See application file for complete search history.

(56) References Cited

U.S. PATENT DOCUMENTS

| | | | | |
|---|---|---|---|---|
| 4,380,090 A | * | 4/1983 | Ramos | 623/22.2 |
| 4,770,661 A | * | 9/1988 | Oh | 623/22.2 |
| 5,002,577 A | * | 3/1991 | Bolesky et al. | 623/22.25 |
| 5,092,897 A | * | 3/1992 | Forte | 623/22.18 |
| 5,133,763 A | * | 7/1992 | Mullers | 623/22.15 |
| 5,263,988 A | * | 11/1993 | Huebner | 623/22.29 |
| 5,458,649 A | * | 10/1995 | Spotorno et al. | 623/22.27 |

* cited by examiner

*Primary Examiner*—David J. Isabella
(74) *Attorney, Agent, or Firm*—Jonathan D. Feuchtwang

(57) ABSTRACT

A prosthetic acetabular component for a hip joint that is inserted into a bone cavity of the natural acetabulum. The acetabular component consists of an articulating component and a constraining component. The articulating component has a hemispherical or dome shape that defines a hemispherical cavity for receiving a femoral ball of a femoral hip stem. The constraining component has a body that connects to the articulating component to capture the femoral ball within the cavity of the articulating component. A locking mechanism connects the constraining component to the articulating component.

16 Claims, 5 Drawing Sheets

CONSTRAINED ACETABULAR LINER

FIELD OF THE INVENTION

The invention relates to a hip joint prosthesis and, more particularly, to a prosthetic acetabulum for a hip joint.

BACKGROUND

Acetabular prostheses generally consist of two separate components, an acetabular shell or cup and an acetabular insert or liner. The shell has a hemispherical shape and is affixed and embedded into a cavity formed in a natural acetabulum of a patient. The insert has a hemispherical shape to mate with an internal cavity of the shell. A low friction bearing surface is formed along a spherical cavity in the insert and is adapted to articulate with a femoral ball of a hip stem.

Typically, the shell is made of a biocompatible metal or metal alloy, and the insert is made of a polymer, such as ultrahigh molecular weight polyethylene. Regardless of the materials or geometries, these two components are generally locked together with the shell encompassing the external surface of the insert. Once the shell is embedded in bone of the natural acetabulum, the insert is ready to receive the femoral ball.

One disadvantage with acetabular prosthesis is that prior bipolar hip prostheses can experience impingement, subluxation, and even dislocation after being implanted in the patient. For instance, the spherical femoral ball of the hip stem can become dislocated from the acetabular component. This dislocation can occur from various reasons, such as trauma to the leg or abnormal twisting of the leg. In some instances, an additional surgical procedure is required to remedy dislocation of a prosthetic hip.

Due to the occurrence of impingement, subluxation, and other problems, it is desirable to have an acetabular insert that inhibits subluxation and dislocation of the femoral ball from the socket. In some designs, the insert is configured to have more than a hemispherical shape. In other words, the insert encloses and captures more than half of the femoral ball within the spherically shaped cavity of the insert itself. Prior patents illustrate an effort to design an insert with a spherically shaped cavity to capture the femoral ball.

U.S. Pat. No. 4,642,123 entitled "Ball and Joint Socket Bearing for Artificial Joint" to Noiles teaches, in one embodiment, an acetabular shell having two coaxial pin members and an acetabular liner having more than a hemisphere in one plane. The liner is rotatable within a spherical cavity of the shell about the coaxial pin members. In other embodiments, a retaining ring is used in conjunction with the shell and liner.

U.S. Pat. No. 4,871,368 entitled "Artificial Acetabulum" to Wagner teaches a one-piece acetabular liner that is mounted in a socket of an acetabular shell. The liner has an extension that extends in an asymmetric relation about a polar axis. This extension is laterally positioned and serves to prevent dislocation of the femoral head from the socket upon extreme deflections of the hip joint.

U.S. Pat. No. 5,002,577 entitled "Variable Position Acetabular Cup" to Bolesky et al. teaches an acetabular prosthesis having a shell, a liner, and an adaptor ring. The shell and liner have a symmetrical shape while the adaptor ring has a non-symmetrical shape. This adaptor can be mounted on the shell in a plurality of positions to change the position of the symmetrical liner after the shell is secured in the acetabulum.

U.S. Pat. No. 5,800,555 entitled "Acetabular Cup Bearing Liner" to Gray teaches a bearing liner formed with a rim that defines an opening to a concave bearing surface that encompasses more than a hemisphere. A channel is formed at the opening of the cavity to permit elastic deformation of the liner to allow the femoral ball to pass into the cavity. A locking component engages the liner to inhibit elastic deformation and capture the femoral ball.

It, therefore, would be advantageous to provide an acetabular prosthesis that provides an increase range of motion with respect to the femoral ball and reduces the occurrence of impingement, subluxation, and dislocation of the femoral ball from the acetabular insert.

SUMMARY

The present invention relates to a hip joint prosthesis and, more particularly, to a prosthetic acetabular component for a hip joint. The acetabular component is adapted to be connected with an acetabular shell to form an acetabular prosthesis. This prosthesis is inserted into a bone cavity of the natural acetabulum.

In one embodiment, the acetabular component generally consists of an acetabular articulating component and an acetabular constraining component. The articulating component generally has a hemispherical or dome shape extending between outer and inner surfaces that define a hemispherical cavity for receiving a femoral ball of a femoral hip stem. The outer surface has a convex shape and is adapted to engage an inner surface of an acetabular shell. The inner surface has a concave shape with a smooth articulating surface adapted to articulate with the femoral ball. An annular rim extends around an outer perimeter of the articulating component along a base portion. This base portion includes a distal end with an annular platform or surface that provides an entrance way or opening into the cavity of the articulating component.

The constraining component is adapted to constrain or capture the femoral ball within the cavity of the articulating component. Specifically, the constraining component has a body with a half moon wedge shape. From a top view, this shape is generally ring shaped or semi-circular. From a side view, this shape is generally triangular. A proximal or top portion of the constraining component includes an annular platform or surface that is shaped and sized to correspond to the shape and size of the annular platform of the articulating component. These two platforms contact so the constraining component forms an extension to the base portion of the articulating component. A distal or bottom portion of the constraining component includes a sloped surface that extends from a first edge to a second edge. When the constraining component is attached to the articulating component, the first edge is adjacent the hemispherical cavity and the second edge is adjacent the outer surface of the articulating component.

The constraining component is adapted to engage and connect or lock with the articulating component. Specifically, a locking mechanism locks the constraining component to the articulating component. This locking mechanism can have various configurations. In one embodiment, a plurality of cylindrical bores extends into both the constraining and articulating components. A first set of bores extends into the base portion through the annular platform, and a second set of bores extends through the body of the constraining component. These two sets of bores are shaped, sized, and spaced to align while the constraining component is positioned against the articulating component. A screw or other device can be positioned through both sets of bores to hold the components together. In another embodiment, a plurality of passages extends into the articulating component. These passages receive and lockingly engage corresponding projections that extend outwardly from the constraining component.

As one feature, the constraining component captures and constrains the femoral ball while simultaneously providing the hip stem with a wide range of motion. The body of the constraining component does not fully extend circumferentially around the base portion of the articulating component. During range of motion of the femoral hip stem, a neck or body of the stem will not impinge against the body of the constraining component. The body is rotationally positioned and then attached to the articulating component to constrain the femoral ball yet not impede its range of motion.

As another feature, in one embodiment, the locking mechanism enables the constraining component to be removeably connected to the articulating component. As such, the constraining component can be attached, detached, and reattached to the articulating component.

Further, the constraining component can be positioned in a variety of different positions around the base portion of the articulating component. These different positions circumferentially extend around a partial portion or entire portion of the base portion. As such, the constraining component can be attached in a plurality of different circumferential positions around the articulating component for optimal range of motion.

Other features and advantages are shown in the accompanying drawings and discussed in connection with the drawings.

DETAILED DESCRIPTION

Figure 1:
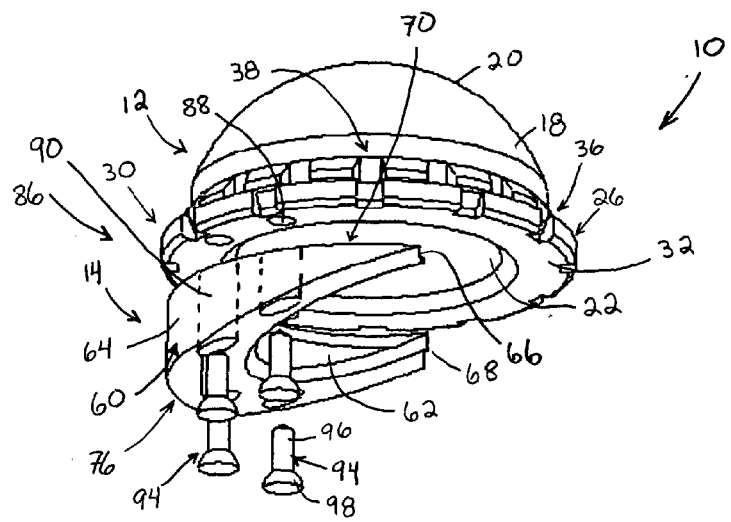
FIG. 1 is an exploded view of the acetabular component of the present invention.
Figure 2:
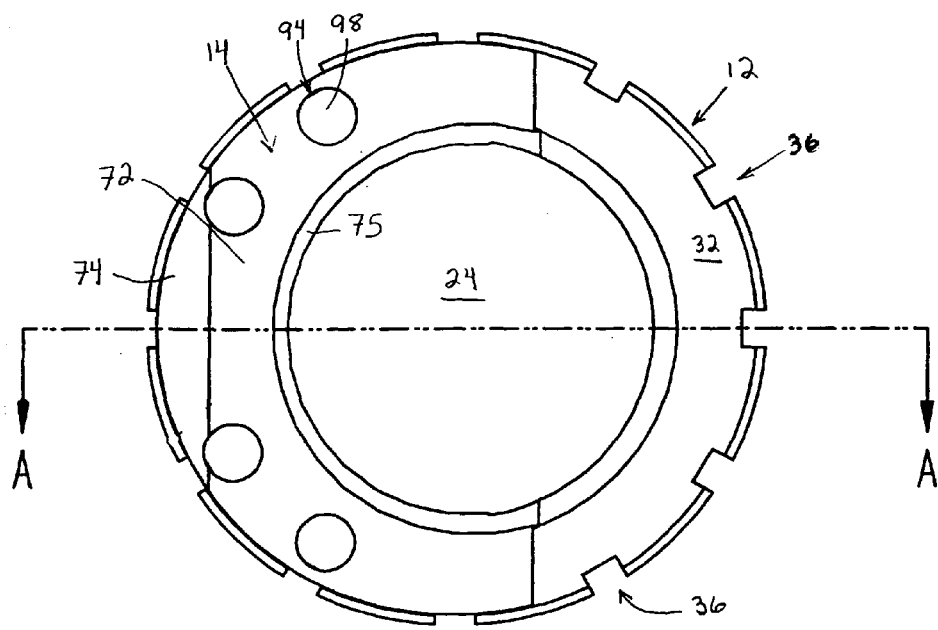
FIG. 2 is a bottom view of an assembled acetabular component of FIG. 1.
Figure 3:
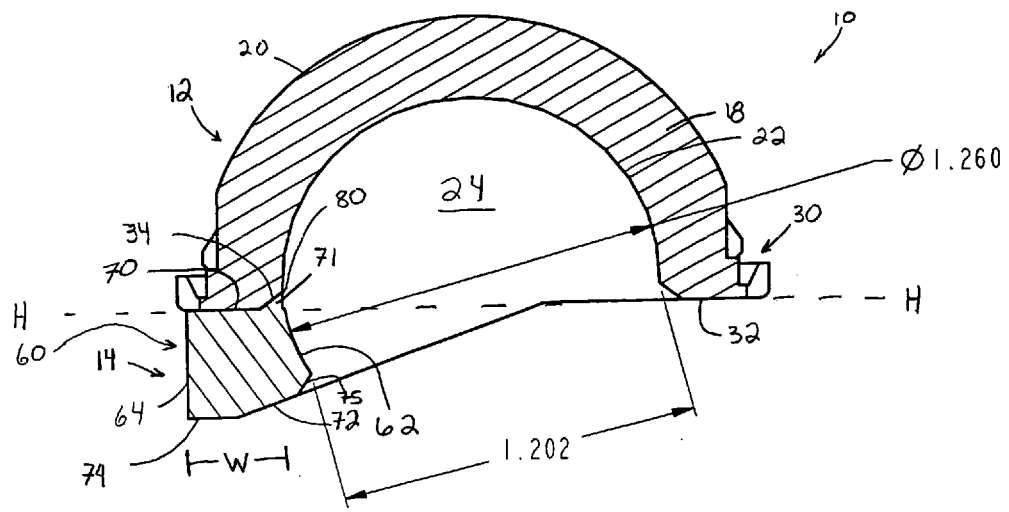
FIG. 3 is a cross-sectional view taken through lines A—A of FIG. 2.
Figures 4, 5:
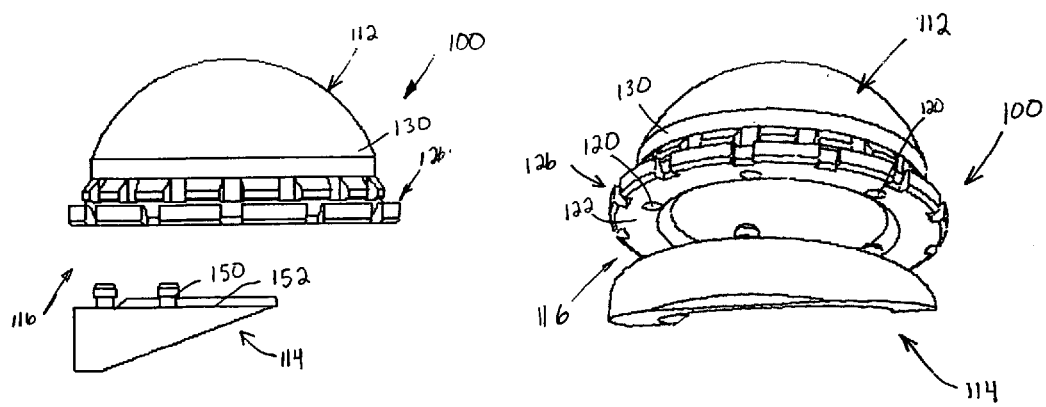
FIG. 4 is an exploded view of an alternate embodiment of the acetabular component of the present invention.
FIG. 5 is another exploded view of the acetabular component of FIG. 4.
Figure 7:
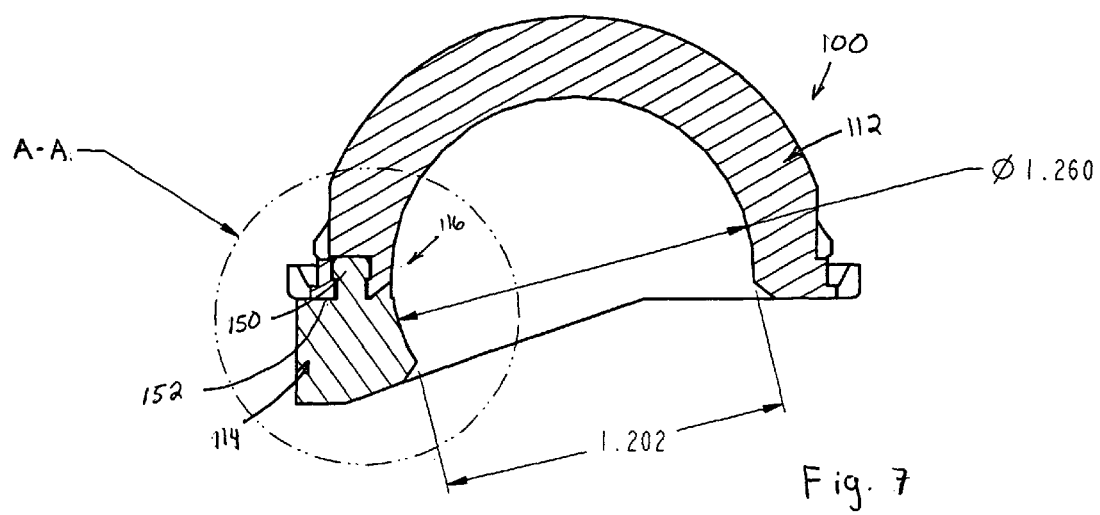
FIG. 7 is a cross-sectional view taken through lines A—A of FIG. 6.
Figure 6:
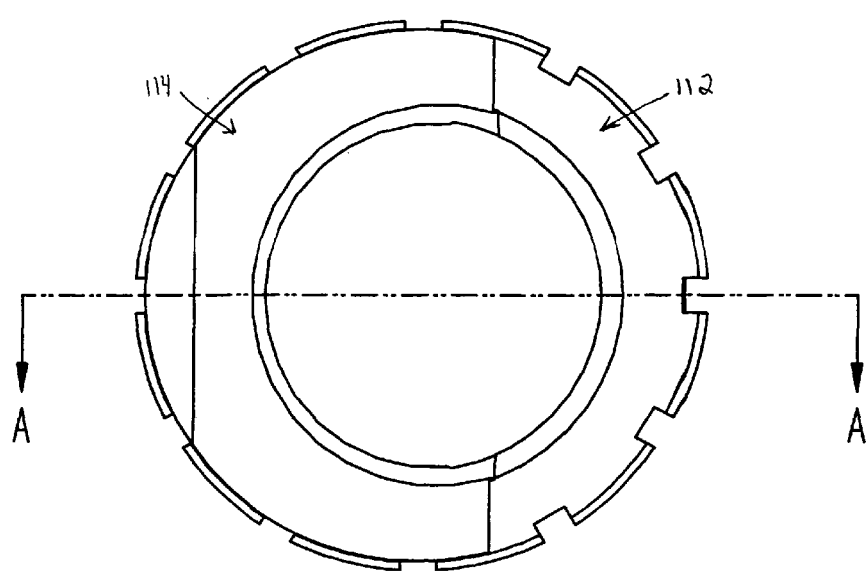
FIG. 6 is a bottom view of an assembled acetabular component of FIG. 4.

Looking to FIGS. 1–3, the acetabular component 10 generally consists of an acetabular articulating component 12 and an acetabular constraining component 14. Acetabular component 10 can be used as an acetabular insert that connects with a separate acetabular shell or without the shell and adapted to function simultaneously as both a shell and insert. The acetabular component, for example, can be cemented and/or screw retained in the natural acetabulum of a patient.

Articulating component 12 generally has a hemispherical or dome shaped body 18 with an outer surface 20 and inner surface 22. The inner surface 22 defines a hemispherical cavity 24 for receiving a femoral ball of a femoral hip stem. Inner surface 22 has a concave shape with a smooth articulating wall or surface adapted to articulate with the femoral ball. The outer surface 20 has a hemispherical or dome shape with a smooth surface that is adapted to engage an inner surface of an acetabular shell. An annular rim 26 extends around an outer perimeter of the articulating component along a base portion 30. This base portion includes a distal end with an annular platform or ring-shaped surface 32 that provides an entrance way or opening into the cavity 24 of the articulating component 12. Platform 32 has a planar surface that circumferentially extends around the entire base portion. A sloped ledge or shoulder 34 (FIG. 3) is adjacent platform 32 and forms a transition into cavity 24.

A first set of notches or recesses 36 is evenly spaced circumferentially around an outer edge of base portion 30. A second set of notches or recesses 38 is evenly spaced circumferentially around outer surface 20 and above notches 36. Notches 38 are adapted to engage and lock with the shell. Both sets of notches have polygonal shapes, but these notches can have various shapes and sizes known in the art. Further, the articulating component 12 can have various configurations and connect to an acetabular shell in various ways. For example, the articulating component can be spherical, hemispherical, or other shapes. U.S. Pat. No. 6,129,765 entitled "Locking Mechanism for Acetabular Cup" to Lopez et al. teaches a locking mechanism for an acetabular cup and is fully incorporated herein by reference.

In one exemplary embodiment, component 14 has a body 60 with a half moon wedge shape. From a bottom view (FIG. 2), body 60 generally forms a semi-circular or partial ring shape. Body 60 has a circular inner wall 62 and a circular outer wall 64. These walls are separated to provide the body with a width "W" shown in FIG. 3. This width is generally equal to the width of platform 32 on the base portion 30 of the articulating component 12. Preferably, walls 62 and 64 have a smooth surface with a spherical contour. Two ends 66 and 68 form an end of a tapered portion of body 60. Body 60 has a top wall or surface 70 formed as a partial annular or circular platform. Surface 70 is planar and adapted to seat against platform 32. A lip 71 (shown in FIG. 3) extends upwardly from surface 70 and forms part of the spherical contour of inner wall 62. Preferably, surface 70 is shaped and sized to correspond to the shape and size of platform 32. A bottom wall or surface 72 is oppositely disposed from surface 70. From a bottom view, this surface 72 has a partial annular or circular shape. From a side view, this surface 72 has a tapered or sloped shape. As seen in FIGS. 2 and 3, a planar surface 74 is adjacent surface 72 on one side, and sloped surface 75 is adjacent surface 72 on another side. As seen in FIG. 1 from a perspective view, body 60 has a triangular shape. Preferably, the body has a constant, gradual, and symmetric taper from a radial edge 76 to ends 66 and 68.

As best shown in FIG. 3, articulating component 12 forms a hemisphere. Platform 32 of base portion 30 extends along a hemispherical dashed line H—H. Surface 70 of constraining component 14 seats against platform 32. Both of these surfaces are planar and form a flush contact. Constraining component 14 forms an extension to articulating component 12. Body 60 extends below the hemispherical line H—H when the articulating and constraining components are connected together to form an acetabular component 10 having more than a hemisphere. More particularly, as shown in FIG. 3, inner surface 22 of articulating component 12 forms a spherical cavity. Inner wall 62 of constraining component 14 forms a partial spherical surface that provides a continuous spherical extension to surface 20. This extension extends below line H—H and captures and retains the femoral ball of a femoral hip stem. Preferably, the interface 80 between surface 22 and wall 62 is smooth, uninterrupted, and seamless.

As shown in FIGS. 1 and 2, a locking mechanism 86 connects the constraining component 14 to the articulating component 12. A first set of bores 88 extends into the platform 32 of base portion 30 of the articulating component. Preferably, these bores are cylindrical and partially extend into the body 60 but not through the body. A second set of bores 90 extends into and through constraining component 14. Bores 90 extend through surfaces 70 and 72. Further, preferably these bores 90 are cylindrical to match the size and shape of bores 88. When constraining component 14 is positioned on articulating component 12, these two sets of bores are shaped, sized, and spaced to align with each other. A screw, post, connector or other device 94 can be positioned through both sets of bores to hold the components together. Connector 94 has an elongated cylindrical shaft portion 96 with a head portion 98. Shaft portion 96 can have external threads adapted to threadably engage threads located inside bores 88. Further, head portion 98 can have a recess, indentation, or other means adapted to engage a tool for inserting the connectors into or removing the connectors from bores 88 and 90.

The locking mechanism 86 can have various configurations to perform the function of connecting the constraining component to the articulating component. This locking mechanism can be adapted to permanently connect the constraining component to the articulating component or removeably connect these two components.

Constraining component 14 is adapted to constrain or capture the femoral ball within the cavity 24 of the articulating component 12. The body 60 of the constraining component does not fully extend circumferentially around the base portion 30 of the articulating component. During range of motion of the femoral hip stem, the neck and body of the stem will not impinge against the body 60 of the constraining component. Body 60 can be rotationally positioned around the base portion 30 and then attached to the articulating component to constrain the femoral ball. The position of the constraining component captures the femoral ball yet does not impede the range of motion of the hip stem.

FIGS. 4–8 show another embodiment of an acetabular component 100 that consists of an acetabular articulating component 112 and an acetabular constraining component 114. Components 112 and 114 are generally similar to the articulating component 12 and constraining component 14, respectively, described in connection with FIGS. 1–3, and reference should be made to these figures for a description of components 112 and 114. One difference between components 112 and 114 and components 12 and 14 is the locking mechanism.

Looking to FIGS. 4–8, acetabular component 100 includes a locking mechanism 116 that connects the constraining component 114 to the articulating component 112. A set of bores 120 extends into the platform 122 of base portion 126 of the articulating component 112. Preferably, these bores are cylindrical and partially extend into the body 130 but not through the body. As shown best in FIG. 8, these bores have a first cylindrical section 132 and a second cylindrical section 134. Section 134 has a diameter greater than section 132 to form a cylindrical capture.

Figure 8:
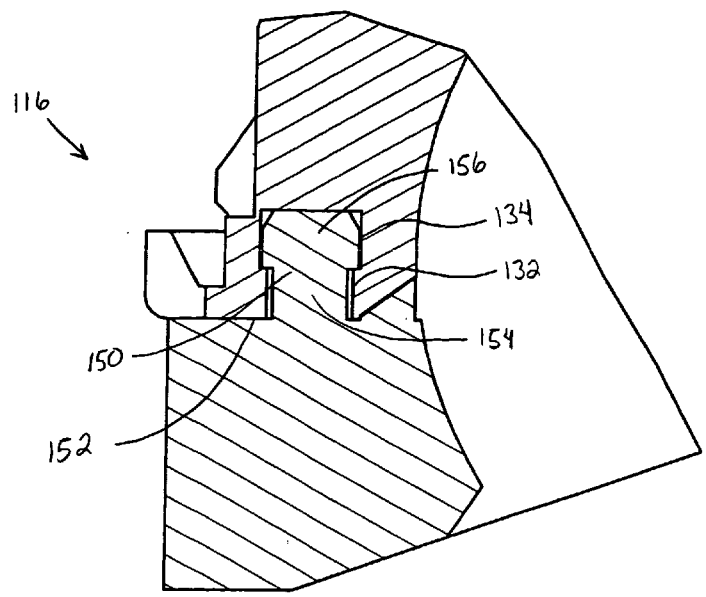
FIG. 8 is an enlarged view taken along circular lines A—A of FIG. 7.
Figures 9, 10:
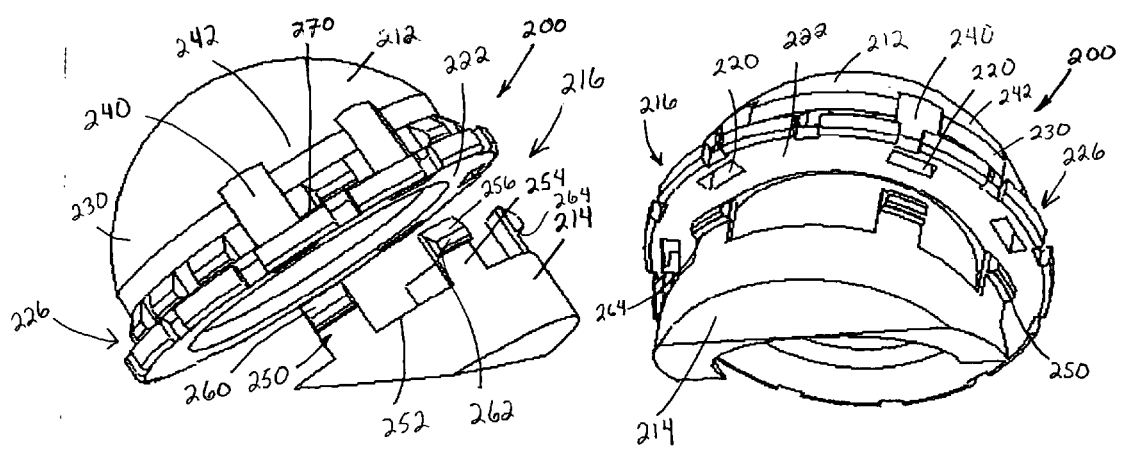
FIG. 9 is an exploded view of an alternate embodiment of the acetabular component of the present invention.
FIG. 10 is another exploded view of the acetabular component of FIG. 9.
Figure 11:
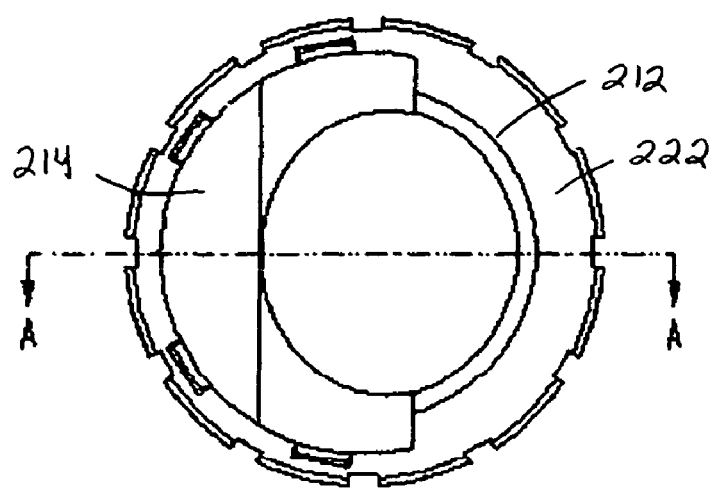
FIG. 11 is a bottom view of an assembled acetabular component of FIG. 9.
Figure 12:
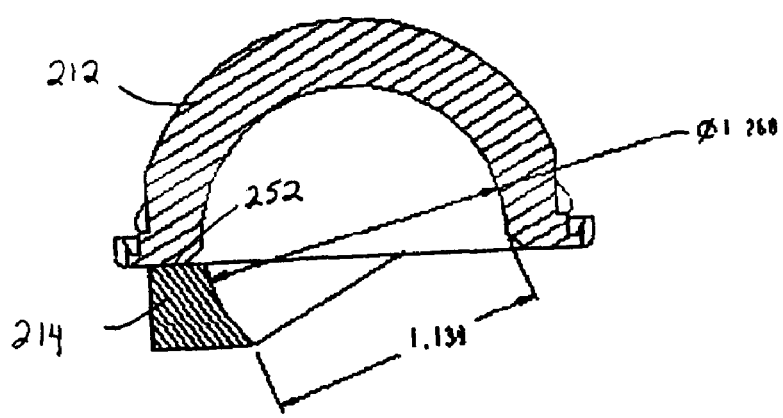
FIG. 12 is a cross-sectional view taken through lines A—A of FIG. 11.

Constraining component 114 includes a plurality of posts or projections 150. These projections extend upwardly from surface 152 and are equally and circumferentially spaced about surface 152. As best shown in FIG. 8, preferably, each post generally has a cylindrical shape with a first cylindrical section 154 or stem section and a second cylindrical section 156 or head section. Section 156 has a diameter greater than section 154 to form an enlarged head.

When constraining component 114 is positioned on articulating component 112, the bores 120 align with corresponding posts 150. The posts are shaped, sized, and spaced to engage or fit into bores 120. As shown in FIG. 8, section 156 is captured in section 134. Posts 150, then, can be adapted to snappingly engage in bores 120.

The locking mechanism 116 can have various configurations to perform the function of connecting the constraining component to the articulating component. This locking mechanism can be adapted to permanently connect the constraining component to the articulating component or removeably connect these two components. Further, the posts 150 can be integrally formed with surface 152 or separate (similar to the exemplary embodiment shown in FIG. 1). Further, the posts are connected to the constraining component, and the bores are in the articulating component. The posts and bores can be switched. Specifically, the posts can be formed as part of the articulating component, and the bores formed as part of the constraining component.

FIGS. 9–12 show another embodiment of an acetabular component 200 that consists of an acetabular articulating component 212 and an acetabular constraining component 214. Components 212 and 214 are generally similar to the articulating component 12 and constraining component 14, respectively, described in connection with FIGS. 1–3, and reference should be made to these figures for a description of components 212 and 214. One difference between components 212 and 214 and components 12 and 14 is the locking mechanism.

Looking to FIGS. 9–12, acetabular component 200 includes a locking mechanism 216 that connects the constraining component 214 to the articulating component 212. A set of passages 220 extends into the platform 222 of base portion 226 of the articulating component 212. Preferably, these passages have a polygonal shape (such as square or rectangular) and completely extend through base portion 226 and body 230. An elongated rectangular channel or recess 240 extends partially into the outer surface 242 of articulating component 212.

Constraining component 214 includes a plurality of posts or projections 250. These projections extend upwardly from surface 252 and are equally and circumferentially spaced about surface 252. Preferably, each post generally has a rectangular shape with a first rectangular section 254 or stem section and a second rectangular section 256 or head section. Section 256 has an enlarged head with a triangular shape from a side view. This head has a sloped surface 260, a flat surface section 262, and a flat bottom surface 264.

When constraining component 214 is positioned on articulating component 212, the passages 220 align with corresponding posts 250. The posts are shaped, sized, and spaced to engage passages 220. Specifically, section 256 fits through a corresponding passage 220 until surface 264 engages on a top surface 270 of base portion 226, and the posts reside in channels 240 of outer surface 242. Section 256 can be adapted to snappingly engage through passages 220.

The locking mechanism 216 can have various configurations to perform the function of connecting the constraining component to the articulating component. This locking mechanism can be adapted to permanently connect the constraining component to the articulating component or removeably connect these two components.

In the embodiments of FIGS. 1–12, the locking mechanism enables the constraining component to connect to the articulating component. This connection can be removeable so the constraining component can be attached, detached, and re-attached to the articulating component.

Further, the constraining component can be positioned in a variety of different positions around the base portion of the articulating component. The base portion can include a plurality of bores or passages that circumferentially extend completely around the base portion or partially around the base portion. As such, the constraining component can be attached in a plurality of different circumferential positions around the articulating component.

Although illustrative embodiments have been shown and described, a wide range of modifications, changes, and substitutions is contemplated in the foregoing disclosure; and some features of the embodiments may be employed without a corresponding use of other features. Accordingly, it is appropriate that the appended claims be construed broadly and in a manner consistent with the scope of the embodiments disclosed herein.

What is claimed is:

1. An acetabular component, comprising:
    an acetabular articulating component having a hemispherical shape and an inner surface forming at least a partial spherical cavity adapted to receive a femoral ball;
    an acetabular constraining component connected to the articulating component and having a spherical surface that is adjacent the inner surface to enlarge the spherical cavity to be more than a hemisphere to partially capture the femoral ball; and
    a locking mechanism formed on both the articulating and constraining components to removeably connect the constraining component to the articulating component;
    wherein constraining component has a semi-circular shape from a bottom view.

2. The acetabular prosthesis of claim 1 wherein the locking mechanism includes a plurality of passages circumferentially disposed along an annular surface of the base portion.

3. The acetabular prosthesis of claim 2 wherein the constraining component engages the passages to connect the constraining component to the articulating component.

4. The acetabular prosthesis of claim 3 wherein the constraining component includes a plurality of projections circumferentially disposed along an annular surface to engage the passages.

5. The acetabular prosthesis of claim 1 wherein the locking mechanism snappingly engages to connect the constraining component to the articulating component.

6. The acetabular prosthesis of claim 1 wherein the locking mechanism threadably engages to connect the constraining component to the articulating component.

7. The acetabular component of claim 1 wherein the constraining compontent has a wedge shape from a side view.

8. The acetabular component of claim 1 wherein the articulating component includes a base portion with a flat annular surface, and the constraining component has a partial ring shape and includes a flat surface seated against the annular surface of the base portion.

9. The acetabular component of claim 8 wherein the constraining component has a triangular shape from a side view.

10. The acetabular component of claim 1 wherein the locking mechanism includes a plurality of passages formed in both the articulating and constraining components and further includes a plurality of screws engageable with the passages to connect the constraining component to the articulating component.

11. The acetabular component of claim 1 wherein the locking mechanism includes a plurality of passages formed in the articulating component and a plurality of projections extending outwardly from the constraining component.

12. The acetabular component of claim 11 wherein the projections snappingly engage with the passages.

13. An acetabular prosthesis adapted to replace a portion of a natural acetabulum, the prosthesis comprising:
    an acetabular shell;
    an acetabular insert connectable to the shell and having an inner surface that forms a spherical cavity to articulate with a femoral ball; and
    a constraining component connectable to the insert, the constraining component having one side with a spherical surface that is continuous with the inner surface to enlarge the spherical cavity to be more than a hemisphere;
    wherein the constraining component is semi-circular and wedge shaped.

14. The acetabular prosthesis of claim 13 wherein the constraining component removeably connects to the acetabular insert.

15. The acetabular prosthesis of claim 14 wherein the constraining component is adapted to capture the femoral ball in the spherical cavity.

16. The acetabular prosthesis of claim 13 wherein the acetabular insert has a base portion, and the constraining component connects to the base portion to form a spherical extension to the acetabular insert to retain the femoral ball.

* * * * *

UNITED STATES PATENT AND TRADEMARK OFFICE
CERTIFICATE OF CORRECTION

PATENT NO. : 7,022,142 B2 Page 1 of 1
DATED : April 4, 2006
INVENTOR(S) : Erin M. Johnson It is certified that error appears in the above-identified patent and that said Letters Patent is hereby corrected as shown below:

<u>Column 8,</u>
Line 8, change "compontent" to -- component --.

Signed and Sealed this

Thirteenth Day of June, 2006

JON W. DUDAS
*Director of the United States Patent and Trademark Office*